(12) United States Patent
Friedrich et al.

(10) Patent No.: US 11,093,027 B2
(45) Date of Patent: Aug. 17, 2021

(54) SYSTEM FOR ASSESSING THE USAGE OF AN ENVISAGED MANUALLY MOVABLE CONSUMER PRODUCT

(71) Applicant: Braun GmbH, Kronberg (DE)

(72) Inventors: Anette Friedrich, Kronberg (DE); Miriam Rietzler, Kronberg (DE); Uwe Bielfeldt, Kronberg (DE)

(73) Assignee: Braun GMBH, Kronberg (DE)

( * ) Notice: Subject to any disclaimer, the term of this patent is extended or adjusted under 35 U.S.C. 154(b) by 0 days.

(21) Appl. No.: 16/785,935

(22) Filed: Feb. 10, 2020

(65) Prior Publication Data

US 2020/0264697 A1 Aug. 20, 2020

(30) Foreign Application Priority Data

Feb. 14, 2019 (EP) .................................... 19157178
Sep. 10, 2019 (EP) .................................... 19196473

(51) Int. Cl.
*G06F 3/01* (2006.01)
*A61B 5/0205* (2006.01)
(Continued)

(52) U.S. Cl.
CPC ............ *G06F 3/011* (2013.01); *A61B 5/0205* (2013.01); *A61B 5/165* (2013.01); *A61B 5/369* (2021.01);
(Continued)

(58) Field of Classification Search
CPC .......... G06F 3/011; G06F 3/016; G06F 3/165; A61B 5/0205; A61B 5/0476; A61B 5/165;
(Continued)

(56) References Cited

U.S. PATENT DOCUMENTS 8,684,941 B2 * 4/2014 Nishioka ................ A61B 5/065
600/493
8,938,477 B1 * 1/2015 Tang ....................... G06F 16/21
707/803
(Continued)

FOREIGN PATENT DOCUMENTS

EP 3528019 A1 8/2019
WO 2006115261 A1 11/2006

OTHER PUBLICATIONS

European search report dated Dec. 9, 2019.
(Continued)

*Primary Examiner* — Abderrahim Merouan
(74) *Attorney, Agent, or Firm* — Kevin C. Johnson; Stefan Schneider (57) ABSTRACT

The present disclosure is concerned with a system for assessing the usage of an envisaged manually movable consumer product by a user. The system has a manually movable consumer product mockup, a simulation subsystem having a display unit for presenting at least partially simulated content and a simulation processing unit for providing the simulated content, a tracking subsystem arranged for tracking at least the motion of the manually movable consumer product mockup with respect to a reference system, a data processing subsystem for receiving usage data. The simulation subsystem is arranged to simulate at least one property or feature of the envisaged manually movable consumer product and to present this property or feature as simulated content via the display unit.

20 Claims, 3 Drawing Sheets

(51) Int. Cl.
*A61B 5/16* (2006.01)
*A61B 5/00* (2006.01)
*G06F 3/16* (2006.01)
*G06T 11/00* (2006.01)
*A61B 5/369* (2021.01)
*A61B 5/021* (2006.01)
*A61B 5/0245* (2006.01)

(52) U.S. Cl.
CPC .............. *A61B 5/443* (2013.01); *G06F 3/016* (2013.01); *G06F 3/165* (2013.01); *G06T 11/00* (2013.01); *A61B 5/021* (2013.01); *A61B 5/0245* (2013.01)

(58) Field of Classification Search
CPC ....... A61B 5/443; A61B 5/021; A61B 5/0245; G06T 11/00
See application file for complete search history.

(56) References Cited

U.S. PATENT DOCUMENTS

| | | | | |
|---|---|---|---|---|
| 9,811,818 | B1* | 11/2017 | Xing | G06F 3/0488 |
| 10,073,953 | B2* | 9/2018 | Xing | G06F 21/6245 |
| 2003/0091967 | A1* | 5/2003 | Chosack | G09B 23/285 |
| | | | | 434/262 |
| 2005/0073531 | A1* | 4/2005 | Kuroki | G06T 19/006 |
| | | | | 345/633 |
| 2007/0002037 | A1* | 1/2007 | Kuroki | G06T 19/006 |
| | | | | 345/418 |
| 2008/0162262 | A1 | 7/2008 | Perkins | |
| 2009/0326556 | A1* | 12/2009 | Diolaiti | A61B 1/00009 |
| | | | | 606/130 |
| 2013/0257899 | A1 | 10/2013 | Baron et al. | |
| 2015/0100290 | A1* | 4/2015 | Falt | A61B 6/10 |
| | | | | 703/2 |
| 2015/0190876 | A1 | 7/2015 | Becker et al. | |
| 2016/0125653 | A1* | 5/2016 | Denis | G06T 7/0004 |
| | | | | 348/90 |
| 2017/0061817 | A1* | 3/2017 | Mettler May | A61B 5/1123 |
| 2017/0178540 | A1* | 6/2017 | Rios | G09B 23/285 |
| 2017/0205702 | A1* | 7/2017 | Word | G03F 1/36 |
| 2017/0252108 | A1* | 9/2017 | Rios | A61B 90/36 |
| 2018/0052216 | A1* | 2/2018 | Vered | G01S 3/143 |
| 2018/0184795 | A1* | 7/2018 | Pai | A46B 5/0095 |
| 2018/0338806 | A1* | 11/2018 | Grubbs | A61B 34/10 |
| 2019/0133893 | A1* | 5/2019 | Recio Saucedo | A61Q 11/00 |
| 2019/0167400 | A1* | 6/2019 | Barnes | A46B 15/0034 |
| 2020/0077892 | A1* | 3/2020 | Tran | A61B 5/6824 |

OTHER PUBLICATIONS

A.Y.C. Nee et al article dated Jan. 1, 2012; "Augmented reality applications in design and manufacturing"; CIRP Annals Manufacturing Technology; vol. 61, No. 2; XP055181739; ISSN: 0007-8506; DOI: 10/1016/j.cirp.2012.05.010.abstract; pp. 657-679.

International Search Report and Written Opinion of the International Searching Authority dated Apr. 17, 2020; European Patent Application No. PCT/IB2020/050965; European Patent Office; Rijswijk, Netherlands.

* cited by examiner

SYSTEM FOR ASSESSING THE USAGE OF AN ENVISAGED MANUALLY MOVABLE CONSUMER PRODUCT

FIELD OF THE INVENTION

The present application is concerned with a system for assessing the usage of an envisaged manually movable consumer product by a user and with a respective method.

BACKGROUND OF THE INVENTION

It is generally known that a property or feature of a manually movable consumer product that is considered for being implemented into the manually movable consumer product can be tested with users for getting user feedback about, e.g., the user-friendliness of the envisaged manually movable consumer product comprising the contemplated property. It is known that the user can be shown pictures of the envisaged manually movable consumer product comprising the contemplated property and the user can in addition get information about the intended usage of the envisaged manually movable consumer product so that the user can provide feedback about the anticipated ease of use. Instead of pictures, the user may be shown a movie about the usage of the envisaged manually movable consumer product having the contemplated property. This may be done by showing an adaptive movie in a virtual reality presented to the user by means of virtual reality goggles, where the movie content adapts to the user's head orientation (i.e. the scene shown on the display of the VR goggles shifts when the head of the user moves). Other assessments of envisaged manually movable consumer products may involve the making of a prototype of the envisaged manually movable consumer product that has the contemplated property for live testing by the user.

There is a general need to provide a system for assessing the usage of an envisaged manually movable consumer product having a contemplated property or feature by a user that allows a larger degree of freedom in assessing the test results than the known systems.

SUMMARY OF THE INVENTION

In accordance with one aspect, a system for assessing the usage of an envisaged manually movable consumer product by a user is provided, the system having a manually movable consumer product mockup intended for being held in at least one of the user's hands during the usage, a simulation subsystem having a display unit for presenting at least partially simulated content and a simulation processing unit for providing the simulated content, a tracking subsystem arranged for tracking at least the motion of the manually movable consumer product mockup with respect to a reference system, the tracking subsystem having at least one tracking data generating unit and a tracking data processing unit for determining position and/or orientation and/or motion data from the tracking data, a data processing subsystem for receiving usage data having at least the position and/or orientation and/or motion data, wherein the simulation subsystem is arranged to simulate at least one property or feature of the envisaged manually movable consumer product and to present this property or feature as simulated content via the display unit; wherein the data processing subsystem is arranged to process at least a portion of the received usage data to compute derived usage data allowing to assess the usage of the envisaged manually movable consumer product; and wherein the data processing subsystem is further arranged to display the derived usage data via the display unit or via a display of a user interaction device.

In accordance with an aspect, a method of assessing the usage of an envisaged manually movable consumer product by a user is provided that comprises the steps:
  using of a manually movable consumer product mockup by a user, the user holding the manually movable consumer product mockup in at least one hand;
  tracking at least the motion of the manually movable consumer product mockup with respect to a reference system, optionally tracking the position and/or orientation and/or motion of a least one body portion of the user with respect to the reference system;
  generating usage data comprising at least the position and/or orientation and/or motion data, optionally generating usage data additionally comprising physiological data from the user;
  generating simulated content using the usage data, the simulated content representing at least one property or feature of the envisaged manually movable consumer product;
  presenting at least the simulated content on a display unit;
  computing derived usage data using at least a portion of the usage data;
  analyzing the derived usage data to assess the usage of the envisaged manually movable consumer product; and
  displaying the derived usage data on the display unit or via a display of a user interaction device.

BRIEF DESCRIPTION OF THE DRAWINGS

The present description will be elucidated by a detailed description of example embodiments and with reference to figures. In the figures
FIG. 3A shows display content prior to the start of usage and FIG. 3B shows display content at the end of usage.

DETAILED DESCRIPTION OF THE INVENTION

In accordance with the present description, a system is provided that allows to assess the usage of an envisaged manually movable consumer product by a user, where at least one property or feature of the envisaged manually movable consumer product is not yet realized and where this property or feature is simulated and is presented to the user by means of simulated content on a display unit. The display unit may in particular comprise a head-mounted display for presenting the simulated content to the user. The simulated content may be overlaid over a real video stream or the simulated content relating to the contemplated property of the envisaged manually movable consumer product may be part of a more extensive simulation that may immerse the user into a completely simulated environment.

The aim of the system is to have the ability to assess a contemplated property or feature of the envisaged manually movable consumer product and to immerse the user into an at least partial virtual reality in which the user experiences this simulated property or feature as a real property or feature. In a simple example, the simulated property is a color of at least a portion of the outer surface of the envisaged manually movable consumer product. In a more sophisticated example, the simulated property is a visual feedback function of the envisaged manually movable consumer product relating to correct handling of the envisaged manually movable consumer product. The simulated property may be provided by the handheld manually movable consumer product itself or by a separate device such as a separate display, e.g. a smartphone. The handheld envisaged manually movable consumer product and the separate device are then considered to represent the envisaged manually movable consumer product. In order to allow this immersion of the user into the at least partial virtual environment, a manually movable consumer product mockup is used that can be held in at least one hand of the user. The manually movable consumer product mockup at least resembles the shape of the envisaged manually movable consumer product at least in the gripping are where the user will hold the manually movable consumer product mockup so that the haptic impression is that of the envisaged manually movable consumer product. The manually movable consumer product mockup may have additional features and may resemble the envisaged manually movable consumer product more completely, depending on the type of virtual environment that will be generated. The manually movable consumer product mockup may be a real manually movable consumer product and the envisaged manually movable consumer product is the same manually movable consumer product but having a further function or different aesthetical appearance.

While it is contemplated that only the envisaged property or feature is presented to the user as simulated content on a display of the display unit during the assessment procedure, the user may also be immersed into a completely simulated environment. That means that the simulation subsystem may present an augmented or mixed reality (AR or MR) or a complete virtual reality (VR) to the user.

In the present description, "user" means a human subject.

"Manually movable consumer product" generally means a product (including a device) that is typically intended for use at home by a single human user and it in particular means a device that is manually operated by the user and that is held in at least one hand of the user when it is used. This shall not exclude that the user may use the manually movable consumer product on another subject. A manually movable consumer product shall in particular mean a manually movable consumer product that is used by the user to treat herself or himself, e.g. by using the manually movable consumer product to treat the skin. The manually movable consumer product may thus be a personal care device. In the context of the present description "personal care" shall mean the nurture (or care) of the skin and of its adnexa (i.e. hairs and nails) and of the teeth and the oral cavity (including the tongue, the gums etc.), where the aim is on the one hand the prevention of illnesses and the maintenance and strengthening of health ("care") and on the other hand the cosmetic treatment and improvement of the appearance of the skin and its adnexa. It shall include the maintenance and strengthening of wellbeing. This includes skin care, hair care, and oral care as well as nail care. This further includes other grooming activities such as beard care, shaving, and depilation. A "personal care device" thus means any device for performing such nurturing or grooming activity, e.g. (cosmetic) skin treatment devices such as skin massage devices or skin brushes; wet razors; electric shavers or trimmers; electric mechanical or light-based epilators; and oral care devices such as manual or electric toothbrushes, (electric) flossers, (electric) irrigators, (electric) tongue cleaners, or (electric) gum massagers.

A manually movable consumer product may either be a consumer device as just described or it may be a functional packaging, e.g. a bottle for applying a fine mist of a cleaning fluid onto a target surface that shall be cleaned. A functional packaging serves two purposes, namely to provide a secure casing for a consumable good (e.g. a cleaning fluid or a perfume or an air refresher or a body lotion etc.) and an interface for manual interaction in order for user-controlled influence of the encased consumable, for example for dispensing the encased consumable.

"Manually movable consumer product mockup" means a three-dimensional object that at least in those parts that will get into contact with the body of the user has the shape of the envisaged manually movable consumer product that shall be assessed. The manually movable consumer product mockup may have one or several properties or features of the envisaged manually movable consumer product that shall be assessed (actually, the manually movable consumer product mockup may have all properties of the envisaged manually movable consumer product but not the simulated property) but because of the simulation abilities of the proposed system, the manually movable consumer product mockup may also be completely non-functional. The manually movable consumer product mockup may have additional functions that are not part of the envisaged manually movable consumer product. E.g. the manually movable consumer product mockup may comprise at least one inertial sensor or an audible feedback unit or a skin contact sensor or the like that may be helpful for performing the assessment procedure. The manually movable consumer product mockup may comprise markers for supporting the tracking of the manually movable consumer product mockup. Markers may be passive markers such as simple color dots or active markers such as sources of electromagnetic energy such as light sources (e.g. LEDs) or sources of acoustic energy (e.g. ultrasonic emitters). The manually movable consumer product mockup may comprise at least one feedback unit such as a haptic feedback unit, an acoustic feedback unit, a thermal feedback unit, an olfactory feedback unit, or a visual feedback unit. This feedback unit may in particular not coincide with a feedback unit the envisaged manually movable consumer product may comprise. But the manually movable consumer product mockup may not be a functional device and a treatment function (e.g. electric shaving of the beard by means of an electric shaving head) may not be available by the manually movable consumer product mockup and instead of a real shaving head an acoustic feedback unit may provide sounds of a real shaving head to immerse the user into the impression of using a "real" manually movable consumer product. The manually movable consumer product mockup may comprise a contact sensor so that, e.g., the acoustic feedback unit is only activated once a treatment head portion of the manually movable consumer product mockup is indeed in contact with the skin.

"Simulated property/simulated feature" means an at least partial appearance of the envisaged manually movable consumer product that is not realized by the manually movable consumer product mockup or a function of the envisaged manually movable consumer product that is not realized by the manually movable consumer product mockup, but which property/feature is added as simulated content and presented to the user via the display unit. The assessment procedure performed with the system as proposed herein shall provide insights into aspects like user-preference, user-friendliness, objective usage improvement, product acceptance, user satisfaction, performance parameters or functional features so that a manually movable consumer product developer can better decide which property or feature to implement into the final manually movable consumer product in which manner so that an improved manually movable consumer product results. The test of the simulated property/feature with the present system allows to test many different embodiments or variants of this property/feature without the need to manufacture numerous real manually movable consumer products having these different properties/features. This more sophisticated assessing ability may lead to manually movable consumer products that generally fulfill consumer needs better than manually movable consumer products developed by known assessment methods. The simulated property/feature is at least one of a manually movable consumer product feedback function, a manually movable consumer product control function, or a manually movable consumer product appearance.

"Usage data" means any type of data relevant for assessment of the usage of the envisaged manually movable consumer product that is realized by the combination of manually movable consumer product mockup and simulated feature. Usage data includes at least position and/or orientation and/or motion data of the manually movable consumer product mockup but may further include motion data of at least one body portion of the user, physiological data of the user and other data such as skin contact data relating to the contact of the user (the skin) with a certain part of the manually movable consumer product mockup.

"Derived usage data" means any data that is based on at least a portion of the usage data and that goes beyond the mere stream of usage data. Derived usage data may thus be usage data sorted for presentation on a display or for a print-out after the test procedure. Derived usage data in particular means data that is based on at least a portion of the usage data and that is processed by means of mathematical operations to provide specific information helpful for the assessment of the usage of the envisaged manually movable consumer product. As one example, derived usage data may relate to the area of skin treated per time period. More generally speaking, derived usage data may relate to the surface treatment. Mathematical methods for processing the usage data may include statistical analysis and machine learning algorithms such as artificial neural networks. As a specific form of derived usage data, the term "surface-related derived usage data" is used and shall mean such derived usage data that can be visualized together with a depiction of the treated surface, such as a path of the manually movable consumer product in space relative to the treated surface and over the surface, an indication of treated surface areas, a map (e.g. a color-coded map) of data as a function of the location on the surface (e.g. a depiction of spots on the treated surface where some unusual usage had occurred such as a treatment time per area above a threshold or a particular increase of the users heart rate while treating this particular location of the surface etc.).

A simulation subsystem in accordance with the present application is a part of the overall system that is responsible for providing simulated content to the user. The simulation subsystem comprises a display unit and a simulation processing unit. The display unit comprises a display for presenting at least partially simulated content to the user. The display may be part of head-mounted virtual reality goggles. The display may in particular be a stereoscopic display allowing the user to immerse into a three-dimensional environment. As is known in the art, a display unit may comprise at least one motion sensor (e.g. including gyroscopes, accelerometers, magnetometers, structured light systems etc.) and optionally also eye tracking sensors. The simulation processing unit is a computing unit that provides the simulated content based on the available information such as absolute or relative positional information of the manually movable consumer product mockup, the relevant body portion(s) of the user, the display unit etc. The simulation subsystem may thus be coupled with the tracking subsystem, the data processing subsystem, or the manually movable consumer product mockup by wired or wireless connection to receive the data necessary for providing the simulated content. As was mentioned, the simulation subsystem may provide only a small added virtual content, e.g. the simulated property/feature of the envisaged manually movable consumer product, but the simulation subsystem may indeed provide a completely simulated environment such as a simulated bathroom and also the body portions of the user may be presented as simulated content.

A tracking subsystem in accordance with the present application provides position and/or orientation and/or motion data relating at least to the manually movable consumer product mockup in particular relative to a reference system. Additionally, the tracking subsystem may provide position and/or orientation and/or motion data of at least one body portion of the user, including the position and/or orientation and/or motion of the user's head, in particular relative to the reference system. In order to provide the mentioned position and/or orientation and/or motion data, the tracking subsystem comprises a tracking data generating unit, which is arranged to track the manually movable consumer product mockup and optionally also to track one or more body portions of the user and further optionally also to track the display unit of the simulation subsystem. The tracking data generating unit may comprise one or more inertial sensors such as accelerometers, magnetometers, or gyroscopes. These inertial sensors may in particular be disposed at the manually movable consumer product mockup or at the user, e.g. by means of one or several wearable devices (including the above-mentioned head-mounted VR goggles). The tracking data generating unit may comprise at least one camera for in particular tracking one or several passive or active markers, but the tracking data generating unit may also use marker-less methods. The camera may in particular be a depth camera or a stereoscopic camera. The tracking data generated by the tracking data generating unit is transmitted to a tracking data processing unit that computes position and/or orientation and/or motion data from the tracking data so that the position and/or orientation and/or motion of the manually movable consumer product mockup and of the at least one body portion of the user are known relative to each other and/or with respect to a reference coordinate system. The position and/or orientation and/or motion data may be determined with respect to an absolute reference system (e.g. a coordinate system fixed with respect to the environment of the user) or to a relative reference system (e.g. a reference system that is fixed to the head of the user).

The system described herein may comprise a measurement subsystem for measuring at least one physiological parameter of the user. The measurement subsystem may comprise at least one physiological sensor unit for measuring the physiological parameter with a given frequency or quasi-continuous. The physiological parameter may be one of a heart rate, a blood pressure, a skin humidity, an intensity of the user's self-talk (muttering), EEG or ECG waves, a galvanic skin response etc. Physiological information may be helpful to assess the usage of the envisaged manually movable consumer product, e.g. the user's heart rate may increase in case the usage of the device is not user-friendly or the intensity of the user's muttering may increase for the same reasons and thus causes stress or unease. The physiological sensor unit may in particular be disposed at a user-wearable device.

The system as described herein comprises a data processing subsystem that receives a temporal sequence of usage data, which means at least position and/or orientation and/or motion data relating to at least the manually movable consumer product mockup and optionally to at least one body portion of the user, and which data processing subsystem is arranged to process at least a portion of the usage data to compute derived usage data. Derived usage data may be stored in a memory unit for later analysis or for later comparison with another set of derived usage data. The data processing device may be arranged to present derived usage data on a display or to print out the derived usage data. The data processing subsystem may be arranged to automatically compare different sets of derived usage data stemming from different assessment procedures in which different variants of the simulated property of the envisaged manually movable consumer product were tested. Usage data received by the data processing subsystem may comprise additional data such as physiological data measured by a measurement subsystem or contact data measured by a contact sensor disposed in the manually movable consumer product mockup.

Derived usage data may also include skin area covered per time period by the head of a manually movable consumer product intended for skin treatment. This may be considered as performance data of the manually movable consumer product usage. Derived usage data may also include the number of treatment head movements of the manually movable consumer product per time period, the angulation of the hand of the user relative to the arm of the user or relative to the body portion etc.

The data processing subsystem may in particular be arranged to process the usage data so as to determine surface-related derived usage data, to depict the treated surface on a display and to overlay a visualization of surface-related derived usage data onto the depiction of the treated surface on the display during and/or after the treatment session. The treated surface may be a body surface, e.g. a leg or an arm or a portion of the oral cavity, or the treated surface may be a part of a room. The data processing subsystem may be further arranged to display other derived usage data on the display, e.g. the current amount of treated surface area as a percentage value or the total time of the treatment session. Other derived usage data may be shown on the display as a number, a table, a graph etc.

Figure 1:
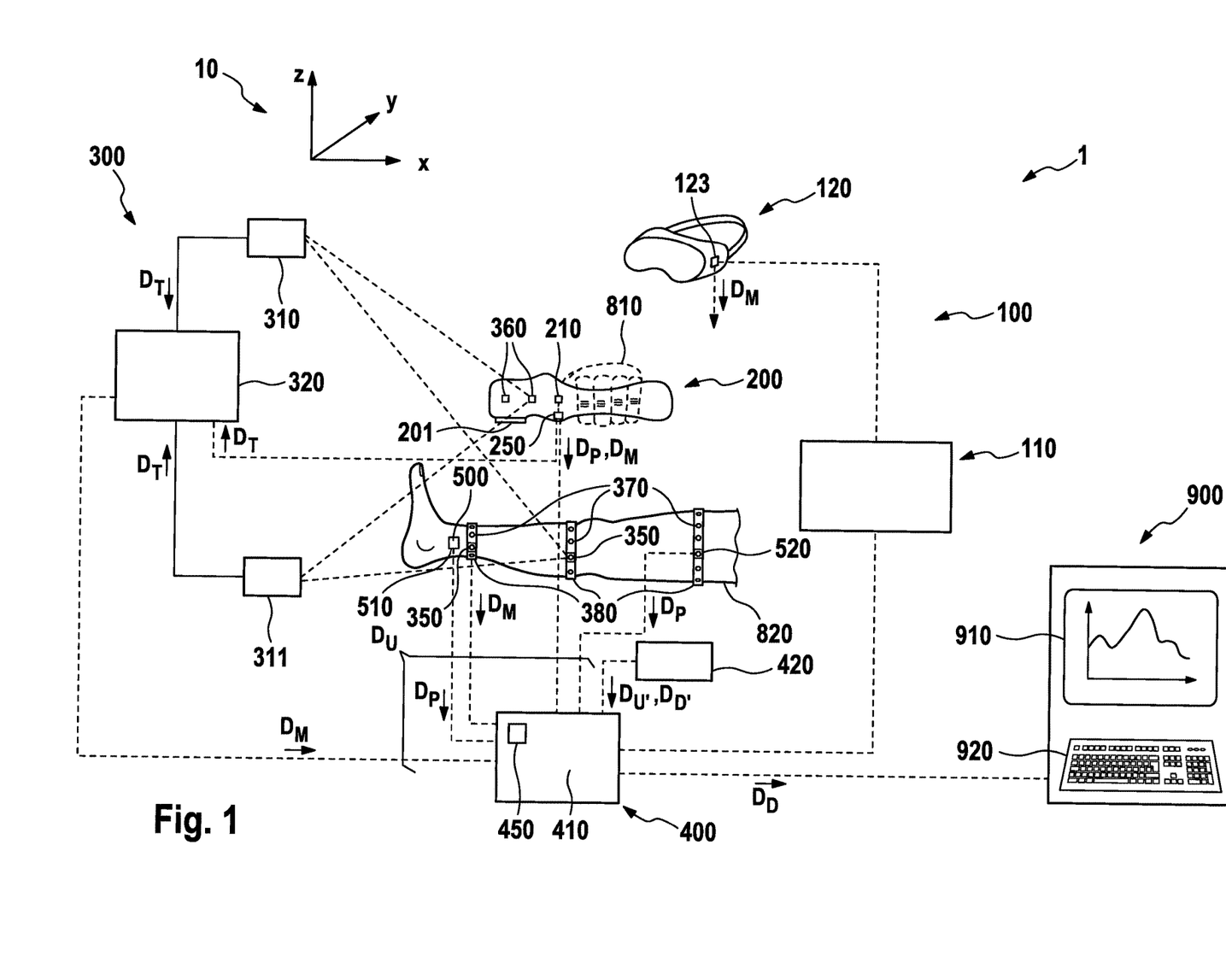
FIG. 1 is a schematic depiction of an example system in accordance with the present disclosure.

FIG. 1 is a schematic depiction of an example system 1 in accordance with the present disclosure. The system 1 comprises a simulation subsystem 100, a manually movable consumer product mockup 200, a tracking subsystem 300, and a data processing subsystem 400. The simulation subsystem 100 comprises a simulation processing unit 110 for generating simulated content that will be shown on a display unit 120, as will be explained in more detail with respect to FIG. 2. The display unit 120 is here shown as a virtual reality headset as one possible embodiment. The display unit 120 may comprise at least one inertial sensor unit 123 for generating linear acceleration data and/or angular rate data and/or orientation data in up to nine axes.

The manually movable consumer product mockup 200 is arranged for being handheld by a user—a hand 810 of a user is indicated in dashed lines. The manually movable consumer product mockup 200 may comprise a treatment head 201 that is intended to be in contact with a body portion 820 of the user during the simulated treatment session. The manually movable consumer product mockup 200 may in particular comprise at least one inertial sensor unit 210 such as a one-, two- or three-axis accelerometer, gyroscope and/or magnetometer in order to determine linear and/or angular accelerations and/or orientation of the manually movable consumer product mockup in a 3-dimensional space along up to nine axes. The output of the inertial sensor unit 210 may be calibrated or converted into values relating to a reference coordinate system 10. The manually movable consumer product mockup 200 may also comprise a transmitter unit or transceiver unit 250 for transmitting data from the inertial sensor unit 210 to a receiver as will be explained in more detail below. If realized as a transceiver unit 250, the transceiver unit 250 may also be arranged to receive data so that the manually movable consumer product mockup 200 may use the received data for respective actions (e.g. feedback actions to the user) of the manually movable consumer product mockup 200 as will be explained in more detail with respect to FIG. 2. A body portion 820 of the user is here shown in a non-limiting manner as a leg, which leg—despite being shown in solid lines—is of course not part of the system 1. While it is referred herein typically to a body portion of the user, this shall not exclude that the user whose usage of the envisaged manually movable consumer product is assessed by means of the disclosed procedure involving the manually movable consumer product mockup uses the manually movable consumer product mockup on a body portion of another subject or on a mockup body portion.

The system 1 also comprises a tracking subsystem 300, which comprises at least one tracking data generating unit 310, 311 and a tracking data processing unit 320. In some embodiments, the tracking subsystem 300 comprises passive or active markers 360 (e.g. passive visual markers or active IR emitting markers, e.g. IR LEDs) that are arranged at the manually movable consumer product mockup 200 and/or markers 370 that are arranged at a body portion 820 to be treated. The tracking data generating unit 310, 311 may then comprise at least one camera, e.g. a stereoscopic camera, that is arranged to track the visual markers 360, 370 in the 3-dimensional space, in particular with respect to the 3-dimensional space spanned by the three coordinates x, y, z of the reference system 10. The tracking data generating unit 310, 311 may comprise more than one camera, e.g. two, three, four, five etc. cameras so that it is assured that the manually movable consumer product mockup and optionally also the treated body portion 820 can be tracked in the 3-dimensional space essentially without non-visible areas. When using cameras, the described motion capturing may use markers on the objects to be tracked (manually movable consumer product mockup and body portion or complete user) or marker-less motion capturing (e.g. based on anatomical landmarks or other patterns or on silhouette-tracking). Instead of cameras or in addition to cameras (or other technologies), the tracking subsystem may use further motion capturing technologies such as at least one inertial sensor unit 350 (e.g. comprising accelerometers, gyroscopes and/or magnetometers) to determine motion and orientation of at least the manually movable consumer product mockup 200 in 3D space with up to 9 axes. In this context, the respective inertial sensor units 123, 210, 350 may be disposed at or in the manually movable consumer product mockup 200, as was already explained, but also at the body portion 820 to be treated or at various body parts of the user. Further, all other elements used in the simulation may be equipped with markers or inertial sensors, e.g. the hand 810 of the user may be equipped with another inertial sensor unit. The display unit 120 may comprise a sensor unit 123 for transferring position and/or motion and/or orientation data $D_M$ to a receiver (the receiver being, e.g., be disposed in the data processing subsystem 400). The inertial sensor unit 350 may be placed at the body portion 820 to be treated, e.g., by means of adhesive stripes or by means of wearable devices 380, as is indicated in FIG. 1. As the body portion 820 to be treated may comprise various parts (e.g. lower leg and upper leg) that may be movable with respect to each other, two or more inertial sensor units 350 may be placed at the body portion 820. Alternatively or additionally to what was discussed so far, the tracking subsystem 300 may comprise at least one magnet that generates a basically known magnetic field (i.e. quantitatively known with respect to the reference system) and magnetometers may then be placed at or in the manually movable consumer product mockup 200 or at the body portion 820 so that direction of the magnetic field and strength of the magnetic field provide an absolute position in the reference system. Such inertial sensor units 123, 210, 350 may be equipped with wireless data transmission technology (e.g. Bluetooth™ or the like) or may be wire-connected to a data receiver (e.g. provided at the tracking data processing unit 320). Alternatively or additionally, the tracking subsystem 300 may make use of ultrasound emission-based tracking technology (e.g. one or several ultrasound emitters that are placed in or at the manually movable consumer product mockup 200 or at the body portion 820) and respective ultrasound receivers. Alternatively or additionally, the tracking subsystem may make use of IR motion capturing technology. Instead of optically visual markers, IR light sources may be used as markers 360, 370 together with respective IR cameras as tracking data generating units 310, 311 (such as available under the brand Nexonar from soft2tec GmbH, Rüsselsheim, Germany). All other 3D tracking technologies known to the skilled person may be used in an alternative or additional manner as well.

The tracking data processing unit 320 receives tracking data $D_T$ from the tracking data generating unit 310, 311 (while it is here shown that the tracking data generating unit(s) 310, 311 are separate from the manually movable consumer product mockup 200, it shall be understood that the tracking data generating unit may alternatively or additionally be realized at or within the manually movable consumer product mockup 200 or the body portion 820, e.g. by means of inertial sensor units 350 that transmit the relevant tracking data $D_T$ to the tracking data processing unit 320. The tracking data processing unit 320 is arranged to compute from the tracking data $D_T$ position, motion (e.g. velocity and acceleration) and/or orientation data $D_M$ that provide position, motion and/or orientation of the manually movable consumer product mockup 200 and/or of the body portion 820 in the reference system 10.

The system 1 further comprises a data processing subsystem 400 that receives the position, motion and/or orientation data $D_M$ from the tracking data processing unit 320 as so-called usage data $D_U$. The data processing subsystem 400 here comprises a data processing unit 410 and a storage unit 420. In some embodiments, the tracking data processing unit 320 and the data processing subsystem 400 are realized as a single integrated subsystem. Instead of being received by the tracking data processing unit 320, position and/or motion and/or orientation data $D_M$ may be transmitted from respective sensor units 250, 350 at the manually movable consumer product mockup 200 or the body portion 820, respectively, directly to the data processing unit 410, in particular to a receiver or transceiver 450 of the data processing unit 410. Such data transfer may happen in a wireless manner or in a wired manner Such position and/or motion and/or orientation data $D_M$ is then considered as usage data $D_U$ as well.

The data processing unit 410 may be arranged to forward the position and/or motion and/or orientation data $D_M$ to the simulation subsystem 300. But the data processing unit 410 may also process the usage data $D_U$ so that the simulation subsystem 100 can be fed with relevant derived usage data $D_D$ allowing the simulation subsystem to provide via the simulation processing unit 110 simulated content to be shown on the display unit 120. The derived usage data $D_U$ may then include relative positions, motions and/or orientations of the manually movable consumer product mockup 200, the body portion 820 and/or the display unit 120. The process of providing simulated content shall be essentially a "live" process (i.e. real-time), i.e. the user shall not note any relevant delay in between the actions the user performs with the manually movable consumer product and the presentation of the simulated content. This recognition of a "live" process may depend on the envisaged manually movable consumer product that is tested and may be around 1 second or lower, e.g. 100 ms or lower. A delay may thus be in the range of between 0.001 ms and 2 seconds, in particular in the range of between 0.1 ms and 1 second, further in particular in the range of between 1 ms and 500 ms and even further in particular in the range of between 1 ms and 100 ms.

The system 1 may comprise a measurement subsystem 500 that is arranged to determine a physiological parameter of the user by means of a physiological sensor unit 510, 520. The respectively measured physiological data $D_P$ is transferred to the data processing unit 400 as usage data $D_U$. The physiological data $D_P$ that is measured by the physiological sensor unit 510, 520 may be at least one of a heart rate data, EEG data, ECG wave data, skin humidity data, blood pressure data, data relating to the acoustic intensity of self-talk of the user, motion data relating to the user's eyes, galvanic skin response data, facial expression data or facial movement data etc. Such physiological data is measured to add a further layer of understanding of the usage of the envisaged manually movable consumer product into the testing procedure and into the automated analysis or at least into the details of data presentation for later human assessment. The physiological sensor unit 510, 520 may be placed at a body portion 820 to be treated and may be incorporated into a wearable device 380. Eye motion data may be measured by placing a respective sensor into a virtual reality headset. The user may also, e.g., wear a wristband in which a physiological sensor unit is included. A microphone may be used to measure the intensity of self-talk of the user during the simulated usage of the envisaged manually movable consumer product. Obviously, one or several sensors may be used at various positions at the user's body or close to the user's body to measure one or several physiological parameters. Such physiological data can then be connected with other usage data $D_U$ to assess the quality of the usage. Physiological parameters that are indicative of unease or stress of the user during the simulated usage of the envisaged manually movable consumer product provide information about the quality of use of the simulated property or feature, which could then be changed to reduce the unease or stress so that the simulated property or simulated feature that is the focus of the assessment procedure can be realized in a more consumer-friendly manner.

Based on the usage data $D_U$, which means at least position and/or motion and/or orientation data $D_M$ of the manually movable consumer product mockup 200, the body portion 820 and/or the display unit 120 and optionally also physiological data $D_P$, the data processing unit 410 determines derived usage data $D_D$, which includes data that allows an automated and/or human user based assessment of the quality of the simulated usage of the envisaged manually movable consumer product. E.g. the data processing unit 410 may compute the total time that was needed to treat a certain body area or the average stress level of the user during the assessment procedure etc. The data processing unit 410 may comprise a storage unit 420 for storing usage data $D_U$ and/or derived usage data $D_D$ from the current assessment procedure and/or for storing usage data $D_{U'}$ and/or derived usage data $D_{D'}$ from a previous assessment procedure or previous assessment procedures, thus allowing the data processing unit 410 to directly and in an automated manner determine performance parameters of the simulated usage of the envisaged manually movable consumer product comprising a certain simulated property or feature. Derived usage data $D_D$ may include usage data $D_U$ that is assembled and prepared for presentation.

The system 1 may also comprise a user interaction unit 900 that may comprise a display 910 for displaying information such as derived usage data $D_D$ in a user accessible manner and a user interface 920 allowing a user to interact with the user interaction unit 900. The user of the user interaction unit 900 may in particular be a different person than the user of the manually movable consumer product. The user of the user interaction unit 900 may in particular be a product developer who analyses the presented derived usage data $D_D$.

It shall not be excluded that the tracking subsystem 300, the data processing subsystem 400, and the simulation subsystem 100 are together (or at least partially, e.g. excluding the tracking data generating unit 310 and the display unit 120) realized as an integral unit, e.g. they may be realized by a single computer.

Figure 2:
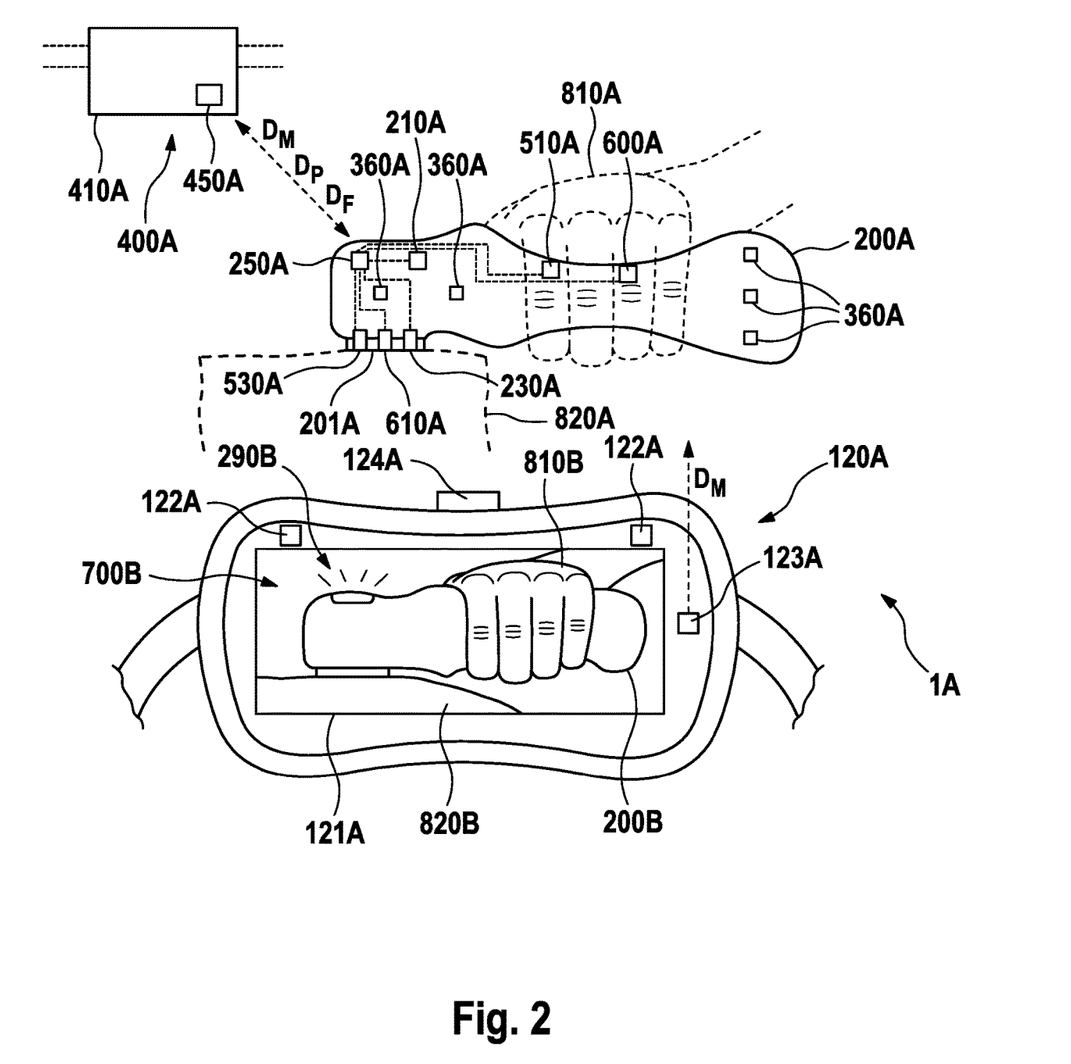
FIG. 2 is a schematic depiction of an example display unit and a manually movable consumer product mockup being part of an example system in accordance with the present disclosure.

FIG. 2 is a depiction of some components of an example system 1A for performing an assessment procedure relating to the usage of an envisaged manually movable consumer product by a user, which shown components here include a display unit 120A, a manually movable consumer product mockup 200A, and a data processing unit 400A. It shall be understood that all other necessary components of the system 1A are considered to be present and optional components may be present. The display unit 120A here is again shown as a virtual reality headset that has a display screen 121A. The user wears the display unit 120A during the test procedure and sees on the display screen 121A displayed content 700B that comprises simulated content 290B, which simulated content in the shown embodiment relates to a visual feedback function of the manually movable consumer product as is indicated by a light illuminating portion on the manually movable consumer product visible on the display screen 121A. In FIG. 2, the displayed content 700B visible on the display screen 121A comprises the manually movable consumer product 200B, the hand 810B of the user and a body portion 820B of the user. In some embodiments, the manually movable consumer product 200B (without the simulated content 290B) and the hand 810B and the body portion 820B visible on the display screen 121A are just the video depictions of the real objects, i.e. video depictions of the manually movable consumer product mockup 200A, the hand 810A, and the body portion 820A. A camera 124A may thus be arranged on the display unit 120A to capture a life video stream of what is visible by the user. The simulation processing unit then only adds the simulated visual feedback function into the video picture as simulated content 290B. In some embodiments, the virtual content 290B includes a deletion of certain features such as markers on the consumer mockup device. In some embodiments, the complete displayed content 700B is virtual content 290B. The simulation subsystem may, e.g., generate images of a virtual bathroom environment together with a virtual body portion and a completely virtual manually movable consumer product.

The display unit 120A may comprise at least one eye tracking sensor 122A for tracking eye movement of the user. The display unit 120A may in particular comprise at least one inertial sensor unit 123A to generate position and/or motion (i.e. velocity and/or acceleration) and/or orientation data $D_M$ that may be transferred to a data processing subsystem 400A, which data processing subsystem 400A may in particular comprise a data processing unit 410A having a receiver unit or transceiver unit 450A for receiving the data $D_M$.

The manually movable consumer product mockup 200A may comprise markers 360A suitable for being detected by a tracking data generating unit, an inertial sensor unit 210A for generating position and/or motion and/or orientation data $D_M$ of the manually movable consumer product mockup 200A and a receiver unit or transceiver unit 250A for transferring data to the receiver unit 450A of the data processing subsystem 400A. Optionally, the manually movable consumer product mockup 200A comprises at least one physiological sensor unit 510A, 530A for determining the value of at least one physiological parameter of the user. Here, a first physiological sensor unit 510A may be disposed at a location on the consumer device mockup 200A where it is possible to measure a physiological parameter at the user's hand 810A (the hand 810A is shown in dashed lines) when the user has grasped the manually movable consumer product mockup 200A in the intended manner and to thus generate physiological data $D_P$. A second physiological sensor unit 530A may be arranged at a treatment head 201A so that a physiological parameter can be measured at the body portion 820A to be treated once the treatment head 201A is in contact with the body portion 820A. The treatment head 201A may also comprise a contact sensor 230A for determining whether the treatment head 201A is in contact with the body portion 820A. While the tracking subsystem may be well equipped and precise enough to determine that the treatment head 201A is with high probability in contact with the body portion 820B, a contact sensor 230A may be used to confirm the contact and to add further precision into the overall tracking performance. All mentioned sensors 210A, 230A, 510A, and/or 530A may be coupled with the receiver unit or transceiver unit 250A so that the measured data can be transmitted to the receiver 450A of the data processing subsystem 400A as usage data.

The manually movable consumer product mockup 200A may comprise a feedback unit 600A so that feedback can be provided to the user in a manner similar or almost identical to the feedback provided by a real manually movable consumer product in use. The feedback unit 600A may be at least one of a thermal, haptic, visual, acoustic, or olfactory feedback unit. The feedback unit 600A may be controlled by a control unit disposed in the manually movable consumer product mockup 200A. One potential use of the feedback unit 600A is to provide a device feedback to the user similar or at least almost identical to the feedback of a real manually movable consumer product. E.g. the manually movable consumer product mockup 200A may not comprise a motor, but the envisaged manually movable consumer product would comprise a motor. Hence, the feedback unit 600A may be realized as a vibrator (e.g. piezoelectric vibrator) that transfers vibrations to the hand 810A of the user in a manner similar to the vibrations of a motor in a manually movable consumer product once switched on. Additionally or alternatively to the feedback unit 600A, a feedback unit 610A may be located at the treatment head 201A. This feedback unit 610A may e.g. be realized as a thermal feedback unit. The manually movable consumer product mockup 200A may be structured to resemble a light-based epilation device, which generates heat in the skin once in use. The thermal feedback unit 610A may be used to simulate this heat generation to render the simulated test procedure more realistic. Instead of being controlled by a control unit in the manually movable consumer product mockup 200A or additionally to such a control, the data processing subsystem 400A may transmit feedback data $D_F$ to the manually movable consumer product mockup 200A to control the feedback unit 600A, 610A.

Figure 3A:
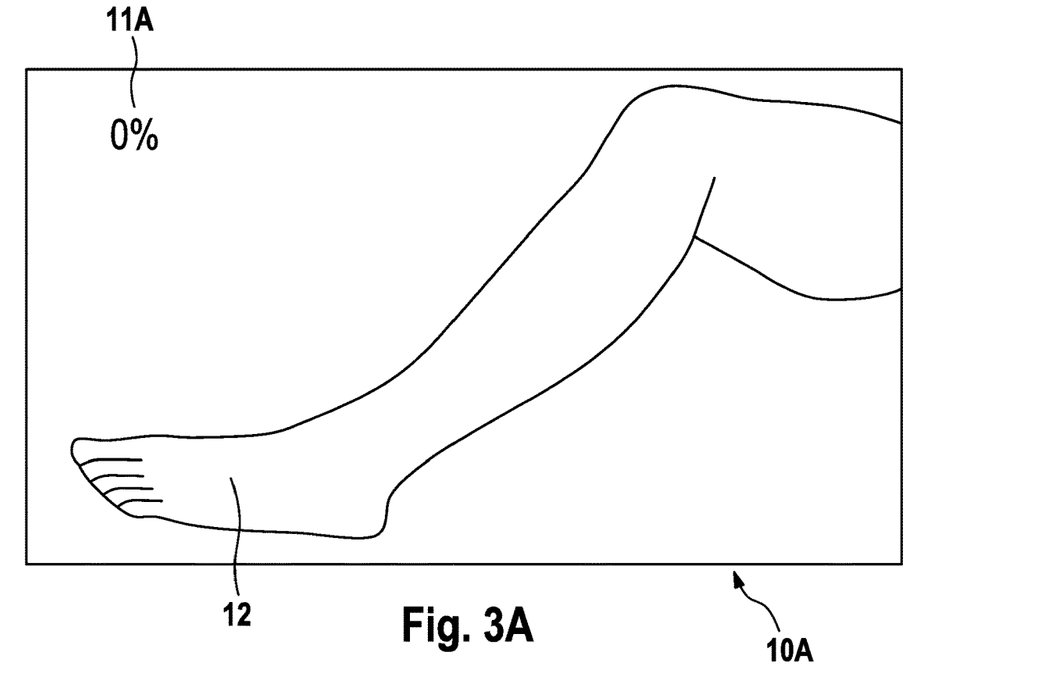
FIGS. 3A, 3B are examples of display content that can be shown to the user or a product developer during or after usage of the manually moveable consumer product, where
Figure 3B:
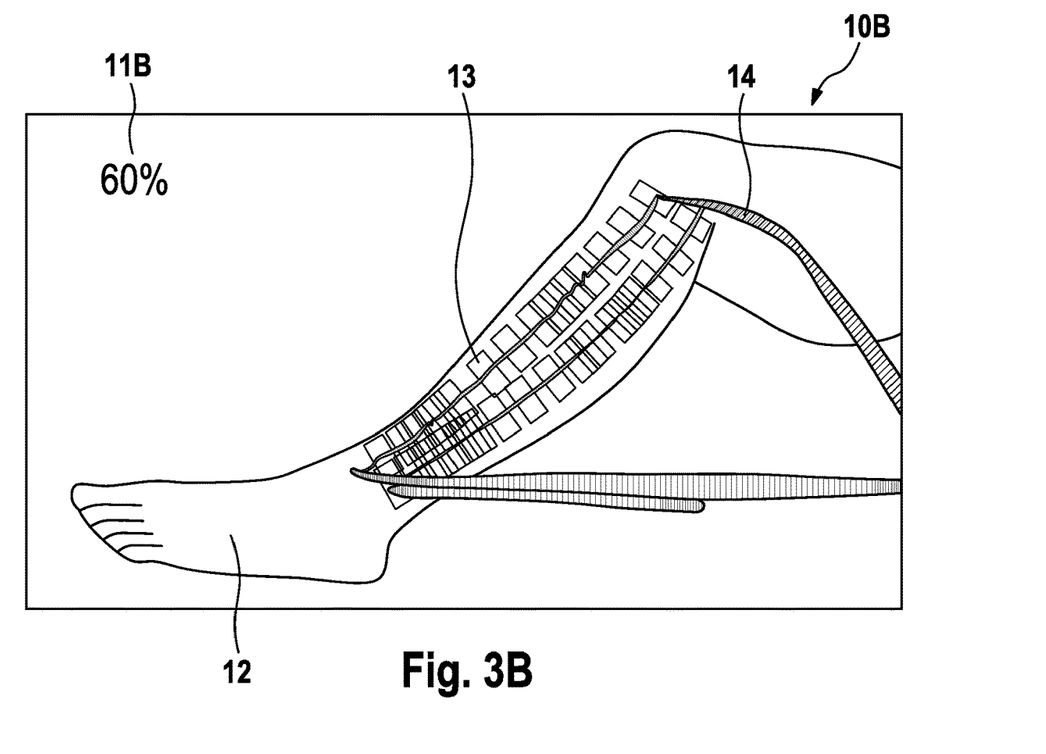

FIGS. 3A and 3B are depictions of the content 10A, 10B of a display controlled by the data processing subsystem. In FIG. 3A, a treated surface 12 is depicted, which surface 12 is in the shown embodiment the surface of a lower leg. One or several values 11A, 11B of derived usage data can be shown on the display. By way of example, values 11A, 11B shown on the display indicate the fraction of treated surface area at the point of time during treatment session to which the displayed content belongs, i.e. 0% in FIG. 3A and 60% in FIG. 3B. Alternatively or additionally, no such value may be shown, or further derived usage data information may be depicted, e.g. by means of single values that may change over time, by means of a table, by means of a graph etc.

In the present example, FIG. 3A shows the display content 10A before usage of the manually moveable consumer product has started and FIG. 3B shows the display content 10B at the end of a usage period (FIG. 3B may also be the display content during a usage period, but for ease of discussion it is here assumed that the display shows the content after the usage session was completed). It can be seen that a visualization of surface-related derived usage data is overlaid over the depiction of the treated surface 12. Surface-related derived usage data that is visualized and displayed may comprise position and velocity information 14, where the path in space of the manually moveable consumer product mockup relative to the treated surface 12 is shown. The width and/or the color or shading of the line that shows the path 14 may be varied to indicate a velocity, where a large width of the path line 14 may indicate a high velocity and a small width of the path line 14 may indicate a low velocity. The shading here follows the width and just underlines the velocity information. In another embodiment, a shading or coloring may provide other information and may relate to a heartbeat of the user or any other surface-related derived usage data.

Further, treated surface areas 13 are shown. The shown example may relate to a light-based skin treatment device as manually moveable consumer product, where the skin of a body portion is treated by a sequence of light pulses. The visualized individual rectangular treated surface regions then each relate to a single light pulse emitted through a rectangular output window of the device. It can be seen that the user has produced overlapping light flashes in some areas and spaced apart light flashes in other areas. This depiction and visualization of surface-related derived usage data allows to assess the usage of the device and to contemplate other feedback mechanisms to the user so that the flashes applied to the skin will be better distributed. A new feedback function may, e.g., include a feedback light that is green in case of a correct speed of the device over the surface and that switches to red in case of a too low or too fast speed over the surface. Such new feedback function of the consumer product can then be checked again with the system proposed herein and the resulting distribution of flashes on the treated surface can be compared with this previous distribution in order to understand whether the new simulated feedback function has improved the result. Instead of a visual feedback, also a haptic feedback function may be tested. The feedback function may be iteratively improved (e.g. combination of visual and haptic feedback function) and at the end of the simulation a sensibly improved device can be designed and manufactured.

Further, it can be seen that some flashes of a first stroke with which the consumer product was mover the surface overlap with neighboring flashes from a second stroke while other flashes have a gap in between. It may now be contemplated that a new feedback function is simulated that tells the user to move to the left or right in order to avoid overlapping flashes of strokes on the one hand and also avoids gaps between strokes on the other hand.

At the end of the usage period, the value 11B indicating the fraction of treated surface shows 60%. It shall be envisioned that the display content changes in a time-sequential manner from the display content 10A shown in FIG. 3A to the display content 10B shown in FIG. 3B.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for assessing the usage of an envisaged manually movable consumer product by a user, wherein the envisaged manually movable consumer product is used by the user to treat the user, comprising:

a manually movable consumer product mockup intended for being held in at least one of the user's hands during the usage;

a simulation subsystem comprising a display unit for presenting at least partially simulated content and a simulation processing unit for providing the simulated content;

a tracking subsystem arranged for tracking at least the motion of the manually movable consumer product mockup with respect to a reference system, the tracking subsystem comprising at least one tracking data generating unit and a tracking data processing unit for determining position or orientation or motion data from the tracking data;

a data processing subsystem for receiving usage data comprising at least the position or orientation or motion data;

wherein the simulation subsystem is arranged to simulate at least one not yet realized property or feature of the envisaged manually movable consumer product and to present this property or feature as simulated content via the display unit;

wherein the data processing subsystem is arranged to process at least a portion of the received usage data to compute derived usage data allowing to assess the usage of the envisaged manually movable consumer product; and wherein the data processing subsystem is further arranged to display the derived usage data via the display unit or via a display of a user interaction device.

2. The system in accordance with claim 1, wherein the tracking subsystem is further arranged for tracking the position or orientation or motion of at least one body portion of the user with respect to the reference system.

3. The system in accordance with claim 1, wherein the manually movable consumer product is arranged for treating a surface and the data processing subsystem is arranged to process at least a portion of the received usage data to compute surface related derived usage data.

4. The system in accordance with claim 3, wherein the data processing subsystem is arranged to display a depiction of the surface and to overlay onto the depicted surface a visualization of the surface-related derived usage data.

5. The system in accordance with claim 4, wherein the data processing subsystem is arranged to display the visualization of the surface-related usage data that is overlaid onto the depicted surface as a time-sequential animation.

6. The system in accordance with claim 1, wherein the tracking data generating unit comprises at least one inertial sensor provided at the manually movable consumer product mockup or wherein the tracking data generating unit comprises at least one user wearable unit comprising at least one inertial sensor.

7. The system in accordance with claim 1, wherein the tracking data processing unit is arranged to determine a position or orientation of the manually movable consumer product mockup relative to a body portion of the user or a velocity of the manually movable consumer product mockup relative to a body portion of the user.

8. The system in accordance with claim 1, further comprising a measurement subsystem having at least one physiological sensor unit for measuring a physiological parameter of the user and for transferring measured physiological data as usage data to the data processing subsystem.

9. The system in accordance with claim 8, wherein the at least one physiological sensor unit is provided at the manually movable consumer product mockup or wherein the at least one physiological sensor unit is provided at a user wearable device.

10. The system in accordance with claim 8, wherein the at least one physiological sensor unit is arranged to measure as the physiological parameter at least one of a heart rate, EEG or ECG waves, skin humidity, blood pressure, or intensity of self-talk of the user.

11. The system in accordance with claim 1, wherein the data processing subsystem is arranged to compare usage data received during a current usage session with previously received usage data from an earlier usage session or is arranged to compare derived usage data from the current usage session with derived usage data from a previous usage session.

12. The system in accordance with claim 1, wherein the manually movable consumer product mockup comprises a feedback unit.

13. The system in accordance with claim 12, wherein the feedback unit is at least one of a haptic feedback unit, an acoustic feedback unit, a thermal feedback unit, an olfactory feedback unit, or a visual feedback unit.

14. The system in accordance with claim 1, wherein the manually movable consumer product mockup comprises at least one contact sensor unit.

15. The system in accordance with claim 14, wherein the manually movable consumer product mockup is arranged to transmit contact data as usage data to the data processing subsystem via a data transmission unit.

16. The system in accordance with claim 1, wherein the simulated at least one property or feature comprises at least one of a manually movable product feedback function, a manually movable consumer product control function, or a manually movable consumer product appearance.

17. A method of assessing the usage of an envisaged manually movable consumer product by a user, wherein the envisaged manually movable consumer product is used by the user to treat the user, comprising the steps:

using a manually movable consumer product mockup by a user, the user holding the manually movable consumer product mockup in at least one hand;

tracking at least the motion of the manually movable consumer product mockup with respect to a reference system;

generating usage data comprising at least the position and/or orientation and/or motion data;

generating simulated content using the usage data, the simulated content representing at least one not yet realized property or feature of the envisaged manually movable consumer product;

presenting at least the simulated content on a display unit;

computing derived usage data using at least a portion of the usage data;

analyzing the derived usage data to assess the usage of the envisaged manually movable consumer product; and displaying the derived usage data on the display unit or via a display of a user interaction device.

18. The method in accordance with claim 17, where the manually moveable consumer product is arranged for treating a surface, the method comprising the further step of displaying a depiction of the treated surface and of overlaying a visualization of surface-related derived usage data onto the depicted surface.

19. The method in accordance with claim 17, further comprising tracking the position and/or orientation and/or motion of a least one body portion of the user with respect to the reference system.

20. The method in accordance with claim 17, wherein generating usage data additionally comprises generating physiological data from the user.

* * * * *